US006858754B2

(12) United States Patent
Borgmeier

(10) Patent No.: US 6,858,754 B2
(45) Date of Patent: Feb. 22, 2005

(54) METHOD FOR THE PRODUCTION OF ACRYLIC ACID BY HETEROGENEOUSLY CATALYZED PARTIAL PROPANE OXIDATION

(75) Inventor: Frieder Borgmeier, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/476,567

(22) PCT Filed: May 2, 2002

(86) PCT No.: PCT/EP02/04794

§ 371 (c)(1),
(2), (4) Date: Nov. 4, 2003

(87) PCT Pub. No.: WO02/090308

PCT Pub. Date: Nov. 14, 2002

(65) Prior Publication Data

US 2004/0138500 A1 Jul. 15, 2004

(30) Foreign Application Priority Data

May 7, 2001 (DE) .......................................... 101 22 027

(51) Int. Cl.[7] ................................................. C07C 51/16
(52) U.S. Cl. ....................... 562/547; 562/542; 562/543; 562/545; 562/606; 502/305; 502/311
(58) Field of Search ................................. 562/512, 542, 562/543, 545, 546, 457; 502/300, 305, 311, 312

(56) References Cited

U.S. PATENT DOCUMENTS 5,380,933 A * 1/1995 Ushikubo et al. ............ 562/549
6,166,241 A * 12/2000 Kayou et al. ................ 558/318

FOREIGN PATENT DOCUMENTS

| DE | 198 35 247 | 2/1999 |
| DE | 100 33 121 | 1/2002 |
| DE | 100 46 672 | 3/2002 |
| DE | 100 51 419 | 4/2002 |
| DE | 101 19 933 | 10/2002 |
| EP | 0 361 372 | 4/1990 |
| EP | 0 608 838 | 8/1994 |
| EP | 0 895 809 | 2/1999 |
| EP | 0 962 253 | 12/1999 |
| EP | 1 090 684 | 4/2001 |
| WO | 00/29105 | 5/2000 |
| WO | 00/29106 | 5/2000 |

* cited by examiner

*Primary Examiner*—Johann Richter
*Assistant Examiner*—Karl J. Puttlitz
(74) *Attorney, Agent, or Firm*—Oblon, Spivak, McClelland, Maier & Neustadt, P.C.

(57) ABSTRACT

Acrylic acid is prepared by heterogeneously catalyzed partial oxidation of propane by a process in which the steam content of the reaction gas starting mixture is reduced in the course of the process.

7 Claims, 1 Drawing Sheet

Figure 1:
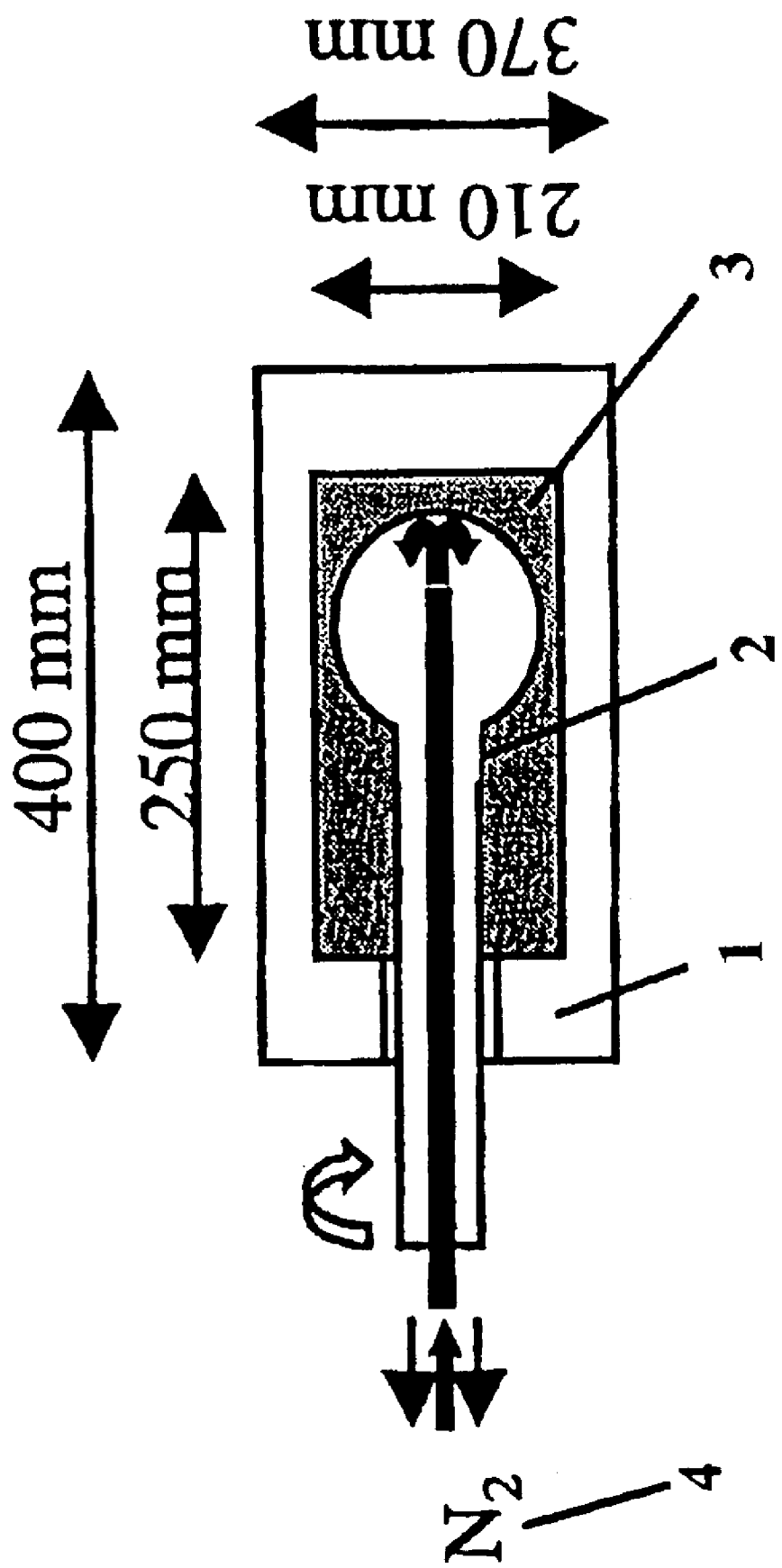

METHOD FOR THE PRODUCTION OF ACRYLIC ACID BY HETEROGENEOUSLY CATALYZED PARTIAL PROPANE OXIDATION

The present invention relates to a process for the preparation of acrylic acid by heterogeneously catalyzed partial oxidation of propane in the gas phase, in which a reaction gas starting mixture containing propane, molecular oxygen and at least one diluent gas is passed at elevated temperatures over a multimetal oxide material having the stoichiometry I $$Mo_1V_bM^1_cM^2_dO_n \qquad (I),$$

where

M$^1$ is Te and/or Sb,

M$^2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, d is from >0 to 1 and n is a number which is determined by the valency and frequency of the elements other than oxygen in (I), and the propane is thereby partially oxidized to acrylic acid.

Processes for the preparation of acrylic acid, a monomer important for the preparation of polymers, by heterogeneously catalyzed partial oxidation of propane over multimetal oxide materials having the stoichiometry I are generally known (cf. for example DE-A 10119933, DE-A 10051419, DE-A 10046672, DE-A 10033121, EP-A 1090684, EP-A 962253, EP-A 895809, DE-A 19835247, EP-A 608838, WO 00/29105 and WO 00/29106).

A common feature of the prior art (cf. for example EP-B 608838, page 4, lines 39/40) and the results obtained therein is that the presence of significant amounts of steam in the reaction gas starting mixture is advantageous both for the catalyst activity and for the selectivity with respect to the acrylic acid formation.

However, the disadvantage of this procedure recommended in the prior art is that the processes from the gas-phase catalytic oxidative preparation of acrylic acid give not pure acrylic acid but a product mixture from which the acrylic acid has to be separated off.

Typically, the product gas mixture of a heterogeneously catalyzed gas-phase partial oxidation of propane to acrylic acid contains, in addition to unconverted propane, secondary components such as propene, acrolein, $CO_2$, CO, acetic acid and propionic acid, as well as the components present as diluent gases, e.g. steam, from which the acrylic acid has to be separated off in order to obtain the pure product.

Owing to the pronounced affinity of acrylic acid to water (the superabsorbers used in babies' diapers are polymers based on acrylic acid), the abovementioned separation task is all the more complicated the larger the amount of steam which was present as diluent gas in the gas-phase oxidation.

The presence of large amounts of steam also promotes the undesired formation of propionic acid as a byproduct, which, owing to its similarity to acrylic acid, can be separated from the latter only with extreme difficulty.

A process for the heterogeneously catalyzed partial oxidation of propane to acrylic acid which requires the presence of steam as a diluent gas only in a small amount, if at all, and in which the catalyst activity and the selectivity with respect to the acrylic acid formation are nevertheless satisfactory would therefore be preferable.

Accordingly, we have found a process for the preparation of acrylic acid by heterogeneously catalyzed partial oxidation of propane in the gas phase, in which a reaction gas starting mixture containing propane, molecular oxygen and at least one diluent gas is passed at elevated temperatures over a multimetal oxide material having the stoichiometry I $$Mo_1V_bM^1_cM^2_dO_n \qquad (I),$$

where

M$^1$ is Te and/or Sb,

M$^2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, d is from >0 to 1 and n is a number which is determined by the valency and frequency of the elements other than oxygen in (I), and the propane is thereby partially oxidized to acrylic acid, wherein the composition of the reaction gas starting mixture is changed at least once while the process is being carried out, in such a way that the molar proportion of the diluent gas steam contained in the reaction gas starting mixture before the change and relative to the molar amount of propane contained in the reaction gas starting mixture is lower after the change.

The novel procedure is based on the surprising finding that multimetal oxide materials having the stoichiometry I substantially retained their ability to form acrylic acid with high activity and selectivity in the catalytic gas-phase oxidation of propane to acrylic acid in the presence of large amounts of steam as diluent gas if first a specific proportion of steam is present in the reaction gas starting mixture for a specific operating time, based on propane contained in the reaction gas starting mixture, and this proportion is then reduced, i.e. the heterogeneously catalyzed gas-phase oxidation of propane under otherwise unchanged operating conditions takes place with higher selectivity with respect to the acrylic acid formation even after the reduction of the proportion of steam in the reaction gas starting mixture than if the heterogeneously catalyzed gas-phase oxidation were to have been carried out continuously with the lower proportion of steam in the reaction gas starting mixture. This statement is also true when the reduction in the proportion of steam is carried out to such an extent that the reaction gas starting mixture no longer contains any steam after the reduction.

In the novel process, the reduction in the proportion of steam is usually at least partly compensated by increasing the proportion of diluent gases other than steam which are present in the novel process. However, the compensation can also be omitted. Such other diluent gases are in particular molecular nitrogen, oxides of carbon, such as CO and $CO_2$, as well as noble gases, such as He or Ar. Propane itself is also suitable as a diluent gas. In this case, the propane is used in the novel process in a superstoichiometric amount, based on the amount of molecular oxygen used.

Usually, mixtures of the abovementioned diluent gases are used. They are usually inert in the novel process, i.e. they undergo substantially no chemical change when the novel process is carried out.

In the novel procedure, the molar reduction in the proportion of steam can of course also be completely compensated or even overcompensated by an equivalent increase in the molar proportion of inert diluent gases other than steam. In the novel process, molecular nitrogen is expediently used as a steam substitute.

As a rule, the novel process is carried out at reaction temperatures of, for example, 200 to 550° C. or from 230 to 480° C. or from 300 to 440° C. In the novel process, the temperature before and after the reduction in the proportion of steam can of course be the same. However, it may also be lower or higher after the reduction in the proportion of steam than before the reduction in the proportion of steam.

The operating pressure (absolute) in the novel process may be 1 atm, less than 1 atm or more than 1 atm. Operating pressures typical according to the invention are from 1.5 to 10, frequently from 1.5 to 4, bar. The operating pressure may be either kept constant or varied during the novel process, i.e. the operating pressure may be higher or lower before the novel reduction in the proportion of steam than thereafter.

In the novel process, the change, required according to the invention, in the composition of the reaction gas starting mixture can of course also be carried out, for example, periodically several times in succession, i.e. after a specific operating time with a reduced proportion of steam, the proportion of steam in the reaction gas starting mixture can be increased again for a specific time and then reduced again, etc.

Pure oxygen, air or air enriched in oxygen or depleted in oxygen may be used as an oxygen source for the novel process.

The propane to be used for the novel process does not have to meet any particularly high requirements with regard to its purity. Propane containing propene as an impurity may also be used for the novel process. Typically, the composition of the reaction gas starting mixture for the novel process is within the following range (molar ratios):

Propane:oxygen:H$_2$O:other diluent gases=1:(0.1–10): (0–50): (0–50).

The abovementioned ratio is preferably 1:(0.5–5):(1–30): (0–30).

According to the invention, the abovementioned ratio is expediently in the range A=1:(0.1–10):(0.1–50):(0–50) before the reduction in the proportion of steam and in the range B=1:(0.1–10):(0–30):(0–30) after the reduction in the proportion of steam.

According to the invention, the range A preferably comprises the molar ratios 1:(0.5–5):(2–30):(0–30) and the range B the molar ratios 1:(0.5–5):(0–20):(0–30).

The abovementioned ranges apply in particular when predominantly molecular nitrogen is used as other diluent gases. The reaction temperature in the novel process is expediently from 250 to 550° C. during the use of the composition range A for the reaction gas starting mixture and is expediently likewise from 250 to 550° C. during the use of the composition range B for said mixture.

Otherwise, the novel process can be carried out in the same way as the procedures described in the prior art evaluated, i.e. the catalyst bed may be a fixed bed, a moving bed or a fluidized bed.

The multimetal oxide materials I to be used according to the invention can be employed either as such (for example after comminution to give a powder or chips) or in the form of moldings for the novel process.

The preparation of multimetal oxide materials I suitable for the novel process is described in the prior art evaluated at the outset. Depending on the preparation process used, the structure of the resulting multimetal oxide tends to be amorphous (as described, for example, in WO 00/29105 and in WO 00/29106) or tends to be crystalline (as described, for example, in EP-A 608838, EP-A 962253, EP-A 895809 and DE-A 19835247).

The preparation is carried out as a rule by producing a very intimate, preferably finely divided dry blend at atmospheric pressure (1 atm) from sources (starting compounds) of the elemental constituents of the multimetal oxide material and then converting said dry blend into an active oxide by thermal treatment under an oxidizing (e.g. air), reducing or inert (e.g. N$_2$) atmosphere or an atmosphere under reduced pressure. However, the multimetal oxide materials I of DE-A 10033121 which are prepared by a hydrothermal method can of course also be used for the novel process.

The shaping of the multimetal oxide materials I to give catalyst moldings suitable for the novel process can be effected, for example, as described in DE-A 10118814 and in DE-A 10119933.

According to the invention, preferably used multimetal oxide materials I are those in which M$^1$ is Te. Furthermore, those multimetal oxide materials I in which M$^2$ is Nb, Ta, W and/or Ti are advantageous for the novel process. Preferably, M$^2$ is Nb. The stoichiometric coefficient b of the multimetal oxide active materials I to be used according to the invention is advantageously from 0.1 to 0.6. In a corresponding manner, the preferred range for the stoichiometric coefficient c is from 0.01 to 1 or from 0.05 to 0.4 and advantageous values for d are from 0.01 to 1 or from 0.1 to 0.6. Particularly advantageous multimetal oxide materials I to be used according to the invention are those in which the stoichiometric coefficients b, c and d are simultaneously in the abovementioned preferred ranges. Further suitable stoichiometries according to the invention are those which are disclosed in the documents of the prior art cited at the outset.

Furthermore, those multimetal oxide materials I whose X-ray diffraction pattern has reflections h and i whose peaks are at the diffraction angles (2θ) 22.2±0.5° (h) and 27.3±0.5° (i) are preferably used for the novel process. The half-width of these reflections may be very small or even very pronounced.

Multimetal oxide materials I whose X-ray diffraction pattern has a reflection k whose peak is at 28.2±0.5° (k) in addition to the reflections h and i are particularly preferred for the novel process.

Preferred according to the invention among the latter in turn are those in which the reflection h is the most intense reflection within the X-ray diffraction pattern and has a half-width of not more than 0.5°, the half-widths of the reflection i and of the reflection k are simultaneously each ≦1° and the intensity P$_k$ of the reflection k and the intensity P$_i$ of the reflection i fulfill the relationship 0.65≦R≦0.85, where R is the intensity ratio defined by the formula $$R=P_i/(P_i+P_k).$$

The X-ray diffraction pattern of these multimetal oxides I preferably has no reflection whose maximum is at 2θ=50±0.3°.

Among these multimetal oxide materials I in turn, those for which 0.67≦R≦0.75 and very particularly preferably those for which R is from 0.70 to 0.75 or R is 0.72 are true are advantageous for the novel process.

The preparation of multimetal oxide materials I which have a reflection i and a reflection k having a half-width of ≦1° and which simultaneously fulfill the relationship 0.65≦R≦0.85 and may have no reflection whose maximum is at 2θ=50±0.3° can be carried out as described in DE-A 10118814 and DE-A 10119933.

Multimetal oxide materials I are used whose reflection i shows that they contain the i-phase. Another crystalline phase in which multimetal oxide materials I can occur is, for example, the k-phase. It is evident from the presence of the reflections h and k and from the presence of a reflection having a maximum position at 50±0.3°.

A specific process for the preparation of multimetal oxide materials I which are to be used according to the invention and in which the proportion of the i-phase is dominant is disclosed, for example, in JP-A 11-43314, DE-A 10118814, DE-A 10119933 and the prior application DE-A 10046672, in which the relevant multimetal oxide materials I are recommended as catalysts for the heterogeneously catalyzed oxydehydrogenation of ethane to ethylene and as catalysts for the heterogeneously catalyzed gas-phase oxidation of propane or propene to acrylic acid.

According to this, a multimetal oxide material which has the stoichiometry (I) and is a mixture of i-phase and other phases (e.g. k-phase) is first produced in a manner known per se and disclosed in most of the prior art publications cited (for example also as described in the prior application DE-A 10033121). In this mixture the proportion of i-phase can then be increased, for example, by removing the other phases, for example k-phase, under a microscope or washing the multimetal oxide active material with suitable liquids. Suitable liquids of this type are, for example, aqueous solutions of organic acids (e.g. oxalic acid, formic acid, acetic acid, citric acid and tartaric acid), inorganic acids (e.g. nitric acid), alcohols and aqueous hydrogen peroxide solutions. Furthermore, JP-A 7-232071 also discloses a process for the preparation of multimetal oxide materials I to be used according to the invention and having a pronounced proportion of i-phase.

In a less systematic manner, multimetal oxide materials I to be used according to the invention and having a pronounced proportion of i-phase are obtainable by the preparation method published in DE-A 19835247. According to this, a very intimate, preferably finely divided, dry blend is produced from suitable sources of their elemental constituents and said dry blend is subjected to a thermal treatment at from 350 to 700° C. or from 400 to 650° C. or from 400 to 600° C. The thermal treatment can be effected in principle under an oxidizing, reducing or inert atmosphere. A suitable oxidizing atmosphere is, for example, air, air enriched in molecular oxygen or air depleted in oxygen. The thermal treatment is preferably carried out under an inert atmosphere, for example under molecular nitrogen and/or noble gas. Usually, the thermal treatment is carried out at atmospheric pressure (1 atm). Of course, the thermal treatment can also be carried out under reduced or superatmospheric pressure.

If the thermal treatment is carried out under a gaseous atmosphere, this may be either stationary or flowing. Altogether, the thermal treatment may take up to 24 hours or more.

The thermal treatment is preferably first carried out under an oxidizing (oxygen-containing) atmosphere (e.g. under air) from 150 to 400° C. or from 250 to 350° C. The thermal treatment is then expediently continued under an inert gas at from 350 to 700° C. or from 400 to 650° C. or from 400 to 600° C. Of course, the thermal treatment can also be effected in such a way that the catalyst precursor material is first tableted (if required after being powdered, and, if required, with addition of from 0.5 to 2% by weight of finely divided graphite) before its thermal treatment and is then subjected to the thermal treatment and subsequently converted into chips.

The thorough mixing of the starting compounds in the preparation of multimetal oxide materials I to be used according to the invention can be effected very generally in dry or in wet form. If it is effected in dry form, the starting compounds are expediently used in the form of finely divided powder and, after mixing and, if required, compaction, are subjected to calcination (thermal treatment).

Preferably, however, the thorough mixing is effected in wet form. Usually, the starting compounds are mixed with one another in the form of an aqueous solution and/or suspension. The aqueous material is then dried and is calcined after the drying. The aqueous material is expediently an aqueous solution or an aqueous suspension. The drying process is preferably carried out immediately after the preparation of the aqueous mixture and by spray-drying (the outlet temperatures are as a rule from 100 to 150° C.; the spray drying can be carried out by the cocurrent or countercurrent method), which requires a particularly intimate dry blend, especially when the aqueous material to be spray-dried is an aqueous solution.

Suitable sources of the elemental constituents when carrying out the preparation of multimetal oxide materials I to be used according to the invention are all those which are capable of forming oxides and/or hydroxides on heating (if necessary in air). Of course, oxides and/or hydroxides of the elemental constituents may also be concomitantly or exclusively used as such starting compounds.

Sources of the element Mo which are suitable according to the invention are, for example, molybdenum oxides, such as molybdenum trioxide, molybdates, such as ammonium heptamolybdate tetrahydrate and molybdenum halides, such as molybdenum chloride.

Suitable starting compounds of the element V which are concomitantly used according to the invention are, for example, vanadyl acetylacetonate, vanadates, such as ammonium metavanadate, vanadium oxides, such as vanadium pentoxide ($V_2O_5$), vanadium halides, such as vanadium tetrachloride ($VCl_4$), and vanadium oxyhalides, such as $VOCl_3$. Other vanadium starting compounds which may be concomitantly used are those which contain vanadium in the oxidation state +4.

Suitable sources of the element tellurium according to the invention are tellurium oxides, such as tellurium dioxide, metallic tellurium, tellurium halides, such as $TeCl_2$, and also telluric acids, such as orthotelluric acid $H_6TeO_6$.

Advantageous antimony starting compounds are antimony halides, such as $SbCl_3$, antimony oxides, such as antimony trioxide ($Sb_2O_3$), antimonic acids, such as $HSb(OH)_6$, and also antimony oxide salts, such as antimony oxide sulfate $(SbO)_2SO_4$.

Niobium sources suitable according to the invention are, for example, niobium oxides, such as niobium pentoxide ($Nb_2O_5$), niobium oxyhalides, such as $NbOCl_3$, niobium halides, such as $NbCl_5$, and also complex compounds of niobium and organic carboxylic acids and/or dicarboxylic acids, e.g. oxalates and alcoholates. The Nb-containing solutions used in EP-A 895 809 are of course also suitable as a niobium source.

Regarding all other possible elements $M^2$, starting compounds which are particularly suitable according to the invention are the halides, nitrates, formates, oxalates, acetates, carbonates and/or hydroxides. Suitable starting compounds are often also their oxo compounds, for example tungstates or the acids derived therefrom. Ammonium salts are also frequently used as starting compounds.

Other suitable starting compounds for the preparation of the novel multimetal oxide materials I are polyanions of the Anderson type, as described, for example, in Polyhedron 6 No. 2 (1987), 213–218. A further suitable literature source for polyanions of the Anderson type is Kinetics and Catalysis 40 No. 3 (1999), 401 to 404.

Other polyanions suitable as starting compounds are, for example, those of the Dawson or Keggin type. According to the invention, those starting compounds which are converted into their oxides at elevated temperatures, either in the presence or in the absence of oxygen, possibly with liberation of gaseous compounds, are preferred.

The multimetal oxide materials I obtainable in the manner described and to be used according to the invention can be used as such [for example in the form of a powder or after tableting of the powder (frequently with addition of from 0.5 to 2% by weight of finely divided graphite) and subsequent conversion into chips] or in the form of moldings for the novel process.

The shaping to give moldings can be effected, for example, by application to a support, as described in the prior application DE-A 10051419.

The supports to be employed for the multimetal oxide materials I to be used according to the invention are preferably chemically inert, i.e. they substantially do not participate in the course of the catalytic gas-phase oxidation of propane to acrylic acid, which is catalyzed by the multimetal oxide material to be used according to the invention.

According to the invention, particularly suitable materials for the supports are alumina, silica, silicates, such as clay, kaolin, steatite, pumice, aluminum silicate and magnesium silicate, silicon carbide, zirconium dioxide and thorium dioxide.

The surface of the support may be either smooth or rough. The surface of the support is advantageously rough since pronounced surface roughness generally results in greater adhesive strength of the applied active material coat.

The preparation of coated catalysts to be used according to the invention can be carried out in a very simple manner by preforming active oxide materials of the formula (I), converting them into a finely divided form and finally applying them to the surface of the support with the aid of a liquid binder. For this purpose, the surface of the support is moistened in a very simple manner with the liquid binder and a coat of the active material is caused to adhere to the moistened surface by bringing into contact with the finely divided active oxide material of the formula (I). Finally, the coated support is dried. In order to obtain a greater coat thickness, the process can of course be repeated periodically. In this case, the coated parent body becomes the new support, etc.

The fineness of the catalytically active oxide material of the formula (I) which is to be applied to the surface of the support is of course adapted to the desired coat thickness. For the coat thickness range of from 100 to 500 $\mu$m, for example, suitable active material powders are those in which at least 50% of the total number of powder particles pass through a sieve having a mesh size of from 1 to 20 $\mu$m and whose numerical proportion of particles having a longest dimension above 50 $\mu$m is less than 10%. As a rule, the distribution of the longest dimensions of the powder particles corresponds to a Gaussian distribution as a result of the preparation. Frequently, the particle size distribution is as follows:

| D ($\mu$m) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

Frequently, the surface roughness $R_z$ of the support is from 5 to 200 $\mu$m, often from 20 to 100 $\mu$m (determined according to DIN 4768, Sheet 1 for using a Hommel tester for DIN-ISO measured surface variables, from Hommelwerke, Germany).

Furthermore, the support material may be porous or nonporous. The support material is expediently nonporous (total volume of the pores $\leq$1% by volume, based on the volume of the support).

The thickness of the active oxide material coat present on the novel coated catalysts is usually from 10 to 1000 $\mu$m. However, it may also be from 50 to 700 $\mu$m, from 100 to 600 $\mu$m or from 150 to 400 $\mu$m. Possible coat thicknesses are also from 10 to 500 $\mu$m, from 100 to 500 $\mu$m or from 150 to 300 $\mu$m.

In principle, any desired geometries of the supports are suitable for the novel process. Their longest dimension is as a rule from 1 to 10 mm. However, spheres or cylinders, in particular hollow cylinders, are preferably used as supports. Advantageous diameters for the spherical supports are from 1.5 to 4 mm. If cylinders are used as supports, their length is preferably from 2 to 10 mm and their external diameter preferably from 4 to 10 mm. In the case of rings, the wall thickness is moreover usually from 1 to 4 mm. Annular supports suitable according to the invention may also have a length of from 3 to 6 mm, an external diameter of from 4 to 8 mm and a wall thickness of from 1 to 2 mm. However, annular supports may also have a geometry of 7 mm×3 mm×4 mm or of 5 mm×3 mm×2 mm (external diameter× length×internal diameter).

Here:
D=Diameter of the particle,
x=the percentage of particles whose diameter is $\geq$D and
y=the percentage of particles whose diameter is <D.

For carrying out the coating process described on an industrial scale, the use of, for example, the principle disclosed in DE-A 2909671 and of that disclosed in DE-A 10051419 is advisable, i.e. the supports to be coated are initially taken in a preferably inclined (the angle of inclination is as a rule $\geq$0° and $\leq$90°, in general $\geq$30° and $\leq$90'°; the angle of inclination is the angle of the center of axis of the rotating container relative to the horizontal) rotating container (for example rotating pan or coating drum). The rotating container transports the supports, for example spherical or cylindrical ones, under two metering apparatuses arranged one after the other a specific distance apart. The first of the two metering apparatuses expediently corresponds to a nozzle (for example an atomizer nozzle operated using compressed air), through which the supports rolling in the rotating pan are sprayed with liquid binder and are moistened in a controlled manner. The second metering apparatus is located outside the atomization cone of the liquid binder sprayed in and serves for feeding in the finely divided oxidic active material (for example via a vibrating conveyor or a powder screw). The support spheres moistened in a controlled manner take up the active material powder fed in, which is compacted by the rolling movement on the outer surface of the support, for example a cylindrical or spherical one, to give a cohesive coat.

If required, the support provided with a base coat in this manner again passes the spray nozzles in the course of the subsequent revolution, is moistened thereby in a controlled manner in order to be able to take up a further coat of finely divided oxidic active material in the course of the further movement, etc. (intermediate drying is as a rule not necessary). Finely divided oxidic active material and liquid binder are generally fed in continuously and simultaneously.

The removal of the liquid binder can be effected after coating is complete, for example by the action of hot gases, such as $N_2$ or air. It is noteworthy that the coating process described results in completely satisfactory adhesion of both the successive coats to one another and of the base coat to the surface of the support.

It is important for the coating method described above that the moistening of the support surface to be coated is carried out in a controlled manner. Briefly, this means that the support surface is expediently moistened in such a way that, although it has adsorbed liquid binder, no liquid phase as such is visible on the support surface. If the support surface is too moist, the finely divided catalytically active oxide material agglomerates to form separate agglomerates instead of being adsorbed onto the surface. Detailed information in this context is to be found in DE-A 2909671 and DE-A 10051419.

The abovementioned final removal of the liquid binder used can be carried out in a controlled manner, for example by evaporation and/or sublimation. In the simplest case, this can be effected by the action of hot gases of corresponding temperature (frequently from 50 to 300° C., often 150° C.). However, only preliminary drying can be effected by the action of hot gases. The final drying can then be carried out, for example, in a drying oven of any desired design (for example a belt drier) or in the reactor. The temperature acting should not be above the calcination temperature used for the preparation of the oxidic active material. Of course, the drying can also be carried out exclusively in a drying oven.

Regardless of the type and geometry of the support, the following may be used as binders for the coating process: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, amino alcohols, such as ethanolamine or diethanolamine, and monofunctional or polyfunctional organic amides, such as formamide. Other advantageous binders are solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. The organic compound is advantageously selected from the abovementioned list of possible organic binders. The organic content of abovementioned aqueous binder solutions is preferably from 10 to 50, particularly preferably from 20 to 30, % by weight. Other suitable organic components are monosaccharides and oligosaccharides, such as glucose, fructose, sucrose or lactose, and polyethylene oxides and polyacrylates.

What is important is that the preparation of coated catalysts suitable according to the invention can be carried out not only by applying the prepared, finely milled active oxide materials of the formula (I) to the moistened support surface. Rather, instead of the active oxide material, a finely divided precursor material thereof can also be applied to the moistened support surface (using the same coating process and binder) and the calcination can be carried out after drying of the coated support.

A suitable finely divided precursor material of this type is, for example, that material which is obtainable by first producing a very intimate, preferably finely divided, dry blend from the sources of the elemental constituents of the desired active oxide material of the formula (I) (for example by spray-drying an aqueous suspension or solution of the sources) and subjecting this finely divided dry blend (if necessary after tableting with addition of from 0.5 to 2% by weight of finely divided graphite) to a thermal treatment for a few hours at from 150 to 350° C., preferably from 250 to 350° C., under an oxidizing (oxygen-containing) atmosphere (e.g. under air) and finally, if required, subjecting it to milling.

After the coating of the supports with the precursor material, calcination is then effected, preferably under an inert gas atmosphere (all other atmospheres are also suitable), at from 360 to 700° C. or from 400 to 650° C. or from 400 to 600° C.

Of course, the shaping of multimetal oxide materials (I) which may be used according to the invention can also be effected by extrusion and/or tableting of both finely divided multimetal oxide materials (I) and finely divided precursor material of a multimetal oxide material (I).

Suitable geometries are spheres, solid cylinders and hollow cylinders (rings). The longest dimension of the abovementioned geometries is as a rule from 1 to 10 mm. In the case of cylinders, their length is preferably from 2 to 10 mm and their external diameter preferably from 4 to 10 mm. In the case of rings, the wall thickness is moreover usually from 1 to 4 mm. Annular unsupported catalysts suitable according to the invention may also have a length of from 3 to 6 mm, an external diameter of from 4 to 8 mm and a wall thickness of from 1 to 2 mm. However, annular unsupported catalysts may also have a geometry of 7 mm×3 mm×4 mm or of 5 mm×3 mm×2 mm (external diameter×length× internal diameter).

Suitable geometries of the multimetal oxide materials (I) to be used for the novel process are of course also all those in DE-A 10101695.

It is essential according to the invention that multimetal oxide materials (I) preferably to be used according to the invention have an X-ray diffraction pattern (in this document, always based on $CuK_\alpha$ radiation) which has reflections h, i and k whose peaks are at the diffraction angles (2θ) 22.2±0.4° (h), 27.3±0.4° (i) and 28.2±0.4° (k), the reflection h being the most intense reflection within the X-ray diffraction pattern and having a half-width of not more than 0.5°, the intensity $P_i$ of the reflection i and the intensity $P_k$ of the reflection k fulfilling the relationship 0.65≦R≦0.85, where R is the intensity ratio defined by the formula $R=P_i/(P_i+P_k)$ and the half-width of the reflection i and that of the reflection k each being ≦1°.

In this document, the definition of the intensity of a reflection in the X-ray diffraction pattern is based on the definition set out in DE-A 19835247, in DE-A 10051419 and in DE-A 10046672.

This means that, if $A^1$ is the peak of a reflection 1 and $B^1$ is the nearest pronounced minimum (minima having reflection shoulders are not taken into account) to the left of the peak $A^1$, in the line of the X-ray diffraction pattern when viewed along the intensity axis perpendicular to the 2θ axis, and, in a corresponding manner, $B^2$ is the nearest pronounced minimum to the right of the peak $A^1$ and $C^1$ is the point at which a straight line drawn from the peak $A^1$ perpendicular to the 2θ axis intersects a straight line connecting the points $B^1$ and $B^2$, then the intensity of the reflection 1 is the length of the linear intercept $A^1C^1$ which extends from the peak $A^1$ to the point $C^1$. The expression minimum means a point at which the slope of a tangent to the curve in a base region of the reflection 1 changes from a negative value to a positive value, or a point at which the slope tends to zero, the coordinates of the 2θ axis and of the intensity axis being used for specifying the slope.

In this document, the half-width is correspondingly the length of the linear intercept between the two intersection points $H^1$ and $H^2$ if a line parallel to the 2θ axis is drawn in the middle of the linear intercept $A^1C^1$, where $H^1$ and $H^2$ are the respective first intersection point of this parallel line with the above-defined line of the X-ray diffraction pattern to the left and right of $A^1$.

An exemplary procedure for determining half-width and intensity is also shown in FIG. 6 in DE-A 10046672.

In addition to reflections h, i and k, the X-ray diffraction pattern of advantageous multimetal oxide materials (I) to be used according to the invention also contains, as a rule, further reflections whose peaks are at the following diffraction angles (2θ):

9.0±0.4° (l),
6.7±0.4° (o) and
7.9±0.4° (p).

It is advantageous if the X-ray diffraction pattern of the catalytically active oxide materials of the formula (I) additionally contains a reflection whose peak is at the following diffraction angle (2θ):

45.2±0.4° (q).

Frequently, the X-ray diffraction pattern of multimetal oxide active materials (I) also contains the reflections 29.2±0.4° (m) and 35.4±0.4° (n).

If the catalytically active oxide material of the formula (I) contains a k-phase, its X-ray diffraction pattern generally also contains further reflections whose peaks are at the following diffraction angles: (2θ):

36.2±0.4° and
50.0±0.4°.

If the reflection h is assigned the intensity 100, it is advantageous according to the invention if the reflections i, l, m, n, o, p, q have the following intensities on the same intensity scale:

i: from 5 to 95, frequently from 5 to 80, in some cases from 10 to 60;
l: from 1 to 30;
m: from 1 to 40;
n: from 1 to 40;
o: from 1 to 30;
p: from 1 to 30 and
q: from 5 to 60.

If the X-ray diffraction pattern contains any of the above-mentioned additional reflections, the half-width thereof is as a rule ≦1°.

All data in this document which are based on an X-ray diffraction pattern relate to an X-ray diffraction pattern produced using Cu-Kα radiation (Siemens diffractometer Theta-Theta D-5000, tube voltage: 40 kV, tube current: 40 mA, aperture V20 (variable), collimator V20 (variable), secondary monochromator (0.1 mm), detector aperture (0.6 mm), measuring interval (2θ): 0.02°, measuring time per step: 2.4 s, detector: scintillation counter).

The specific surface area of multimetal oxide active materials (I) to be used according to the invention is often from 1 to 30 $m^2/g$ (BET surface area, nitrogen).

In the novel process, freshly prepared catalysts to be used according to the invention are preferably first exposed to a reaction gas starting mixture which has a high steam content, based on propane present (i.e. in the composition range A).

If the novel process is carried out at as a fixed-bed oxidation, it is expediently effected in a tube-bundle reactor whose catalyst tubes are loaded with the catalyst. Usually, a liquid, as a rule a salt bath, is passed as a heating medium around the catalyst tubes.

Considered over the reactor, the reaction gas mixture is fed in the catalyst tubes either cocurrently or countercurrently relative to the salt bath. The salt bath itself may flow entirely parallel to the catalyst tubes. However, a transverse flow can also be superposed on said parallel flow. Overall, the salt bath may also execute meandering flow around the catalyst tubes, which flow is cocurrent or countercurrent relative to the reaction gas mixture, considered over the reactor. Tube-bundle reactors suitable for the novel process are disclosed, for example, in EP-A 700714 and EP-A 700893. In the novel process, the propane space velocity over the catalyst load may be, for example, from 10 to 500 l(S.T.P.)/l·h. The space velocity of the reaction gas starting mixture is frequently from 100 to 10 000, often from 500 to 5 000, l(S.T.P.)/l·h.

In the novel process, the reaction gas starting mixture can be preheated to the reaction temperature before being fed to the reaction zone containing the catalysts.

Of course, the novel process gives a product gas mixture which does not consist exclusively of acrylic acid. Rather, in addition to unconverted propane, the product gas mixture contains secondary components, such as propene, acrolein, $CO_2$, CO, $H_2O$, acetic acid, propionic acid, etc., from which the acrylic acid has to be separated.

Since both the amount of steam contained in the product gas mixture and the formation of acetic and propionic acid as byproducts are limited by the novel procedure, this separation can be effected as generally known from the heterogeneously catalyzed gas-phase oxidation of propene to acrylic acid.

This means that the acrylic acid contained can be taken up from the product gas mixture, for example by absorption with a high-boiling inert hydrophobic organic solvent (for example a mixture with diphenyl ether and diphyl, which, if required, may also contain additives, such as dimethyl phthalate). The resulting mixture of absorbent and acrylic acid can then be worked up in a manner known per se by rectification, extraction and/or crystallization to give the pure acrylic acid. Alternatively, the basic separation of the acrylic acid from the product gas mixture can also be effected by fractional condensation, as described, for example, in DE-A 19924532.

The resulting acrylic acid condensate can then be further purified, for example by fractional crystallization (e.g. suspension crystallization and/or layer crystallization).

The residual gas mixture remaining in the basic separation with the acrylic acid contains in particular unconverted propane and possible unconverted propene. This can be separated from the residual gas mixture, for example by fractional rectification under superatmospheric pressure, and then recycled to the novel gas-phase oxidation. However, it is more advantageous to bring the residual gas into contact, in an extraction apparatus, with a hydrophobic organic solvent (for example by passing through said residual gas) which is capable of absorbing the propane and any propene preferentially.

By subsequent desorption and/or stripping with air, the absorbed propane and any propene can be liberated again and can be recycled to the novel process. In this way, economical total propane conversions can be achieved. However, the acrylic acid can of course also be separated from the product gas mixture by the procedure described in DE-A 10059122.

A noteworthy feature of the novel process is that it permits high selectivity with respect to the acrylic acid formation in combination with a reduced steam requirement.

The multimetal oxide materials I to be used according to the invention can of course also be used in the novel process in a form diluted with finely divided, e.g. colloidal, materials, such as silica, titanium dioxide, alumina, zirconium oxide and niobium oxide.

The dilution mass ratio may be up to 9 (diluent):1 (active material), i.e. possible dilution mass ratios are, for example, 6 (diluent):1 (active material) and 3 (diluent):1 (active material). The diluent can be incorporated before and/or after the calcination. If the incorporation is effected before the calcination, the diluent must be chosen so that it is substantially retained as such during the calcination. This is as a rule true, for example, in the case of oxides calcined at correspondingly high temperatures.

Catalysts consumed in the novel process can be regenerated repeatedly by loading with oxygen-containing gases, e.g. air or air depleted in oxygen or enriched with oxygen, to which steam may also have been added, at temperatures≦reaction temperature.

EXAMPLES

A) Preparation of a Multimetal Oxide I Catalyst to be Used According to the Invention 1287.25 g of ammonium metavanadate (77.5% by weight of $V_2O_5$, from G.f.E., Nuremberg, Germany) were dissolved with stirring at 80° C. in 44.6 l of water in a stainless steel container. A clear yellowish solution formed. This solution was cooled to 60° C. and then 1683.75 g of telluric acid (99% by weight of $H_6TeO_6$, from Fluka) and then 5868.0 g of ammonium heptamolybdate (81.5% by weight of $MoO_3$, from Starck) was stirred in in succession in said order while maintaining the 60° C. A deep red solution A formed. In a second stainless steel container, 1599.0 g of ammonium niobium oxalate (21.1% by weight of Nb from Starck, Goslar, Germany) were dissolved at 60° C. in 8.3 l of water to form a solution B. The two solutions A and B were cooled to 30° C. and combined with one another at this temperature, the solution B being stirred into the solution A. Stirring in was effected continuously in the course of 10 minutes. An orange aqueous suspension formed.

This suspension was then spray-dried ($T_{Receiver}$=30° C., $T^{in}$=240° C., $T^{out}$=110° C., duration of drying: 1.5 h, spray tower from Nipolosa). The resulting spray-dried material was likewise orange. 1% by weight of finely divided graphite (sieve analysis: min. 50% by weight<24 μm, max. 10% by weight>24 μm and <48 μm, max. 5% by weight>48 μm, BET surface: from 6 to 13 m²/g) was mixed into the spray-dried material.

The resulting mixture was compacted (compressed) to give hollow cylinders (rings) having the geometry 16 mm×2.5 mm×8 mm (external diameter×height×internal diameter), in such a way that the resulting lateral compressive strength of the rings was about 10 N.

200 g of these rings was calcined in two 100 g portions in succession in a rotary sphere oven according to FIG. 1 (quartz glass sphere having an internal volume of 1 liter; 1=oven housing, 2=rotating flask, 3=heated space, 4=nitrogen/air stream). For this purpose, the content of the rotary sphere oven was heated from 25° C. to 275° C. with a linear heating ramp in the course of 27.5 minutes under an air stream of 50 l(S.T.P.)/h and was kept at this temperature while maintaining the air stream for 1 hour. Heating was then effected from 275° C. to 600° C. with a linear heating ramp in the course of 32.5 minutes, the air stream being replaced by a nitrogen stream of 50 l(S.T.P.)/1. 600° C. and nitrogen stream were maintained for 2 hours and the entire oven was then left to cool to 25° C. while maintaining the nitrogen stream. Black tablets having the composition $Mo_{1.0}V_{0.33}Te_{0.15}Nb_{0.11}O_x$ resulted.

The tablets were dry-milled to a particle size of <100 μm in a Retsch mill. 150 g of the milled material were stirred into 1 500 ml of a 10% strength by weight aqueous $HNO_3$ solution in the course of 7 hours at 70° C. under reflux and the solid was filtered off from the resulting suspension and was washed nitrate-free with water. The filter cake was dried overnight under air at 110° C. in a muffle furnace. The resulting active material had the composition $Mo_{1.0}V_{0.27}Te_{0.12}Nb_{0.13}O_x$.

75 g of the active material powder obtained were applied to 300 g of spherical supports having a diameter of 2.2–3.2 mm (support material=steatite from Ceramtec, Germany, total pore volume≦1% by volume, based on the total support volume; $R_z$=45 μm). For this purpose, the supports were initially taken in a coating drum having an internal volume of 2 l (angle of inclination of the central axis of the drum relative to the horizontal=30°). The drum was caused to rotate at 25 revolutions per minute. About 30 ml of a mixture of glycerol and water (glycerol:water weight ratio=1:3) were sprayed onto the supports over 60 minutes via an atomizer nozzle operated with 300 l(S.T.P.)/h of compressed air. The nozzle was installed in such a way that the spray cone wet the supports transported in the drum by metal driver plates to the uppermost point of the inclined drum, in the upper half of the rolling zone. The finely divided active material powder was introduced into the drum via a powder screw, the powder feed being located inside the rolling zone but below the spray cone. Through periodic repetition of wetting and powder metering, the support provided with the base coat itself became the support in the subsequent period.

After coating was complete, the coated supports were dried for 16 hours at 120° C. in a through-circulation drying oven (from Binder, Germany, internal volume 53 l). Glycerol was removed by a subsequent 2-hour heat treatment at 150° C. under air. A coated catalyst S to be used according to the invention and containing 20% by weight of active material was obtained.

B) Carrying Out the Novel Process and a Comparative Process

In each case 35 g of freshly prepared coated catalyst S were installed in a single-tube reactor (tube length: 140 cm, internal diameter: 8.5 mm, external diameter: 60 mm, V2A stainless steel, catalyst bed length: 54.5 cm, a 30 cm long preliminary bed of steatite beads from Ceramtec (2.2–3.2 mm diameter) additionally for warming up the reaction gas starting mixture, the reaction tube was furthermore finally filled with the same steatite beads after the catalyst zone) which was heated by electric heating mats. At a mat temperature of 350° C., the coated catalyst was installed in the tube reactor in air.

Thereafter, in four experiments W, X, Y and Z independent of one another, four fresh tube reactor catalyst loads were loaded for 48 hours, at a heating mat temperature of 350° C., with the following reaction gas starting mixtures W, X, Y and Z:

W: 3.3% by volume of propane, 10% by volume of $O_2$, 40% by volume of $N_2$, 46.7% by volume of $H_2O$;

X: 3.3% by volume of propane, 10% by volume of $O_2$, 40% by volume of $N_2$, 46.7% by volume of $H_2O$;

Y: 3.3% by volume of propane, 10% by volume of $O_2$, 70% by volume of $N_2$, 16.7% by volume of $H_2O$;

Z: 3.3% by volume of propane, 10% by volume of $O_2$, 86.7% by volume of $N_2$, 0% by volume of $H_2O$.

The residence time (based on the catalyst bed volume) was 2.4 seconds in all cases. The operating pressure was 2 bar absolute in all cases.

At the end of the 48 hours, the reaction tubes were further loaded with the following reaction gas starting mixture compositions while maintaining the residence time, and the following results were obtained after a further operating time of 4 hours (with a single pass through the reaction tube, $T_M$=heating mat temperature used):

W (according to the invention): 3.3% by volume of propane,
10% by volume of $O_2$,
86.7% by volume of $N_2$,
0% by volume of $H_2O$,
$T_M$=390° C.,
propane conversion in a single pass through the reaction tube ($C_P$): 25 mol %,
selectivity $S_{AA}$ of the acrylic acid formation in a single pass through the reaction tube:
50 mol %.

Z (comparison to W): 3.3% by volume of propane,
10% by volume of $O_2$,
86.7% by volume of $N_2$, 0% by volume of $H_2O$,
$T_M$=390° C.,
$C_P$=25 mol %,
$S_{AA}$=40 mol %.

X (according to the invention): 3.3% by volume of propane,
10% by volume of $O_2$,
70% by volume of $N_2$,
16.7% by volume of $H_2O$,
$T_M$=370° C.,
$C_P$=25 mol %,
$S_{AA}$=70 mol %.

Y (comparison to X): 3.3% by volume of propane,
10% by volume of $O_2$, 70% by volume of $N_2$,
16.7% by volume of $H_2O$,
$T_M$=385° C.,
$C_P$=25 mol %,
$S_{AA}$=50 mol %.

The results obtained demonstrate the advantageousness of the novel procedure.

I claim:

1. A process for the preparation of acrylic acid comprising:

passing a reaction gas starting mixture containing propane, molecular oxygen and at least one diluent gas comprising steam over a multimetal oxide material at elevated temperature, wherein the multimetal oxide material has the stoichiometry I $$Mo_1V_bM^1_cM^2_dO_n \qquad (I),$$

where $M^1$ is Te, Sb or both Te and Sb, $M^2$ is at least one element selected from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is 0.01 to 1, c is >0 to 1, d is >0 to 1 and n is a number which is determined by the valency and frequency of the elements other than oxygen in (I), wherein the propane is at least partially oxidized to acrylic acid, said process further comprising changing the composition of said reaction gas starting mixture at least once while the process is being carried out, the change to the composition of said reaction gas starting mixture being such that the proportion of the steam contained in the reaction gas starting mixture, before the change and relative to the molar amount of propane contained in the reaction gas starting mixture, is lower after the change.

2. The process as claimed in claim 1, wherein the following molar ratios are present in the reaction gas starting mixture before the changing:

propane:oxygen:$H_2O$:other diluent gases=1:(0.1–10):(0.1–50):(0–50).

3. The process as claimed in claim 1, wherein the following molar ratios are present in the reaction gas starting mixture after its composition has been changed:

propane:oxygen:$H_2O$:other diluent gases=1:(0.1–10):(0–30):(0–30).

4. The process as claimed in claim 1, wherein the reaction gas starting mixture is passed over the multimetal oxide material at a temperature of from 250° C. to 550° C. before the changing of the composition of the reaction gas starting mixture.

5. A process as claimed in claim 1, wherein the acrylic acid produced by said process is included in a product gas mixture and is recovered from said product gas mixture by absorption with a high-boiling inert hydrophobic solvent.

6. A process as claimed in claim 5, wherein said solvent comprises diphenyl ether.

7. A process as claimed in claim 1, wherein after an operating time with a reduced proportion of steam, the proportion of steam in the reaction gas starting mixture is increased for a time and then reduced again.

* * * * *